United States Patent [19]
De Burgh Bradley et al.

[11] Patent Number: 5,665,356
[45] Date of Patent: Sep. 9, 1997

[54] HUMAN ANTI-RH (D) MONOCLONAL ANTIBODIES

[75] Inventors: Benjamin Arthur De Burgh Bradley, Winterbourne Down; Alan Doyle, Salisbury; Belinda Mary Kumpel, Bristol, all of England

[73] Assignee: The National Blood Authority, Watford, England

[21] Appl. No.: 477,552

[22] Filed: Jun. 7, 1995

Related U.S. Application Data

[62] Division of Ser. No. 57,560, May 6, 1993, Pat. No. 5,487,891, which is a continuation of Ser. No. 469,516, filed as PCT/GB88/00755, Sep. 16, 1988, 1990, abandoned.

[30] Foreign Application Priority Data

Sep. 18, 1987 [GB] United Kingdom ............... 8722018

[51] Int. Cl.$^6$ ............... A61K 39/395; C12N 5/12
[52] U.S. Cl. ............... 424/153.1; 530/358.1; 530/388.25; 424/141.1; 424/130.1; 424/156.1
[58] Field of Search ............... 424/141.1, 130.1, 424/153.1, 156.1; 530/388.1, 388.25; 435/240.27

[56] References Cited

FOREIGN PATENT DOCUMENTS

| | | |
|---|---|---|
| 02511440 | 1/1988 | European Pat. Off. . |
| 2127434 | 4/1984 | United Kingdom . |
| 2145113 | 3/1985 | United Kingdom . |
| WO85/02413 | 6/1985 | WIPO . |
| WO89/02443 | 3/1989 | WIPO . |

OTHER PUBLICATIONS

Bron et al., "Production of Human Monoclonal IgG Antibodies Against Rhesus (D) Antigen", *Proc. Natl. Acad. Sci. USA*, 81:3214–3217 (1984).

Crawford et al., "Production of Human Monoclonal Antibody to Rhesus D Antigen", *The Lancet*, 386–388 (1983).

Doyle et al., "In Vitro Development of Human Monoclonal Antibody-Secreting Plasmacytomas", *Human Immunology* 13:199–209 (1985).

Kumpel et al., "Heterogeneity in the Ability of IgG1 Monoclonal Anti–D to Promote Lymphocyte–Mediated Red Cell Lysis", *Eur. J. Immunol.* 19:2283–2288 (1989).

Kumpel et al., "Human Monoclonal Anti–D Antibodies I. Their Production, Serology, Quantitation and Potential Use as Blood Grouping Reagents", *British J. Haemotology* 71:125–129 (1989).

Kumpel et al., "Human Monoclonal Anti–D Antibodies II. The Relationship between IgG Subclass, Gm Allotype and Fc Mediated Function", *British J. Haemotology* 71:415–420 (1989).

Leader et al., "Human Monoclonal Anti–D with Reactivity Against Category $D^{VI}$ Cells Used in Blood Grouping and Determination of the Incidence of the Category $D^{VI}$ Phenotype in the $D^U$ Population", *Vox. Sang.* 58:106–111 (1990).

Lomas et al., "Tar + Individuals With Anti–D, A New Category D", *Transfusion*, 26(6):S62 (1986).

Lomas et al., "Demonstration of Seven Epitopes on the Rh Antigen D Using Human Monoclonal Anti–D Antibodies and Red Cells from D Categories", *Vox. Sang.* 57:261–264 (1989).

Lowe et al., "A Human–Human Monoclonal Anti–D by Direct Fusion with a Lymphoblastoid Line" *Vox Sang.*, 51:212–216 (1986).

MacDonald et al, "Production and Characterization of Human–Human and Human–Mouse Hybridomas Secreting Rh(D)–Specific Monoclonal Antibodies" *Scand. J. Immun.*, 25:477–483 (1987).

McCann et al., "Production and Use of Human Monoclonal Anti–D Antibodies", *Journal of Immunological Methods*, 115(1):3–15 (1988).

Melamed et al., "Requirements for the Establishment of Heterohybridomas Secreting Monoclonal Human Antibody to Rhesus (D) Blood Group Antigen", *Journal of Immunological Methods*, 104:245–251 (1987).

Mollison et al., Chapter 2 of *Haemolytic Disease of the Newborn*, ed. G. Garraty, 1–32 (1984).

Ono et al., "Preparation of Monoclonal Antibody to Rh(D-)–Positive Antigen", *Chemical Abstract* No. 147012e, vol. 104, No. 17 (28 Apr. 1986) (English abstract of JP 60–136599).

Paire et al., "Establishment of Human Cell Lines Producing Anti–D Monoclonal Antibodies: Identification of Rhesus D Antigen", *Immunol. Lett.*, 13:137–141 (1986).

Thompson et al., "Production of Human Monoclonal IgG and IgM Antibodies With Anti–D(rhesus) Specificity Using Heterohybridomas", *Immunology*, 58:157–160 (1986).

Thomson et al., "Clearance of Rh D–Positive Red Cells With Monoclonal Anti–D", *The Lancet*, 336:1147–1150 (1990).

Tippett, "Sub–Divisions of the Rh (D) Antigen", *Medical Laboratory Science*, 45:88–93 (1988).

Tippett et al., "Observations on Subdivisions of the Rh Antigen D", *Vox Sang.*, 7:9–13 (1962).

*Primary Examiner*—Lila Feisee
*Assistant Examiner*—Minh-Tam Davis
*Attorney, Agent, or Firm*—Burns, Doane, Swecker & Mathis, L.L.P.

[57] ABSTRACT

The present invention provides human monoclonal antibodies having the following essential characteristics: (a) binding to Rh(D) antigen, but not C, c, E or e antigens of the Rh blood group system; (b) being IgG1 proteins; (c) having kappa light chains; (d) being Glm(3) or Glm(1,17) allotype; (e) binding to $D^u$ cells by an indirect antiglobulin test; (f) binding to $D^{IV}$, $D^V$ and $D^{VII}$ variant antigens; and (g) not binding to $D^{VI}$ or $D^B$ variant antigens, which may be employed for Rh-typing of red blood cells and passive immunization to prevent hemolytic disease of the newborn. Such a monoclonal antibody is exemplified by the monoclonal antibodies of cell lines ECACC 87091605 and 87091604 deposited at the European Collection of Animal Cell Cultures, Public Health Laboratory Service Center for Applied Microbiology and Research, Porton Down, Salisbury, Wiltshire, SP4, OJG, England on Sep. 16, 1987.

24 Claims, 2 Drawing Sheets

HUMAN ANTI-RH (D) MONOCLONAL ANTIBODIES

This application is a divisional of application Ser. No. 08/057,560, filed May 6, 1993, now U.S. Pat. No. 5,487,891 which is a continuation of application Ser. No. 07/469,516, filed Apr. 3, 1990 (now abandoned), which was the National Phase of International Application No. PCT/GB88/00755, filed Sep. 16, 1988.

The present invention relates to human monoclonal antibodies to the Rh(D) antigen of human red blood cells. In particular, it relates to such antibodies of the IgG1 sub-class which may be used to detect not only the normal Rh(D) antigen on either D-positive or "weak D" or $D^u$ cells, but also important variants of the Rh(D) antigen.

Of the antigens of the so-called Rh blood group system, the Rh(D) antigen is responsible for some of the most severe reactions following transfusion to a patient with corresponding antibody. Since an Rh(D−) individual with anti-Rh(D) who receives Rh(D+) blood is liable to suffer substantial red blood cell (RBC) destruction due to the Rh(D) phenotype incompatibility, blood of donors and blood transfusion recipients is routinely classified as Rh(D+) or Rh(D−) by agglutination tests with anti-Rh(D) antibody. The Rh phenotype of RBCs is commonly further defined with reference to the Fisher-Race system, which is based on the assumption that the inheritance of the Rh antigens is determined by three pairs of allelic genes, C-c, D-d and E-e, acting at very closely linked loci. According to this theory, a person may inherit a set of three Rh genes from each of his parents (i) C or c, (ii) D or d, (iii) E or e (no d antigen has as yet been identified, but the symbol 'd' is used to indicate the presence of a gene, allelic to the D gene, which does not produce D antigen). For example, an Rh(D+) person may inherit CDe from one parent and cde from the other. The frequencies of the commonest Rh gene combinations as determined with reference to the Fisher-Race system for an English population, together with the 'short symbols' which are used, particularly in speech, are given in Table 1 below.

TABLE I

Frequency of common Rh genes for an English Population

| Short symbol | CDE nomenclature | Frequency (%) |
|---|---|---|
| $R^1$ | CDe | 40.8 |
| r | cde | 38.9 |
| $R^2$ | cDE | 14.1 |
| $R^0$ | cDe | 2.6 |
| $R^{1w}$ | $C^wDe$ | 1.3 |
| r" | cdE | 1.2 |
| r' | Cde | 0.01 |
| $R^z$ | CDE | rarer |
| $r^y$ | CdE | |
| $R^N$ | (C) D (e) | |

Despite expansion over the years, the Fisher-Race system has not been adequate to account for all the reactions that have been observed with the Rh system (Mollison, P. L. (1983) Blood Transfusion In Clinical Medicine, 7th edn., Blackwell Scientific, Oxford). Nevertheless, the World Health Organisation has recommended that in the interest of simplicity and uniformity this nomenclature should be universally adopted and all Rh genotypes given hereinafter are defined on the basis of the conventional Fisher-Race system.

In addition to the need for anti-Rh(D) antibody for Rh-typing of RBCs, such antibody is also importantly required for passive immunisation of Rh(D−) mothers to prevent haemolytic disease of the newborn (HDN). This condition arises in newborn Rh(D+) infants of Rh(D−) mothers previously sensitized to Rh(D) antigen as a result of IgG anti-Rh(D) antibodies crossing the placenta during pregancy and causing foetal RBC destruction. Sensitization of the Rh(D−) mother to Rh(D) antigen may have occurred at the birth of an earlier Rh(D+) child due to some foetal RBCs entering the maternal circulation and being recognised by the maternal immune system. To reduce the incidence of HDN, it is routine practice in the United Kingdom and many other countries to give anti-Rh(D) antibodies to Rh(D−) mothers immediately after the birth of an Rh(D+) infant so that any Rh(D+) RBCs which have entered the maternal circulation are rapidly removed (Mollison, P. L. (1983) cit.; Laros Jr., R. K. (1986), "Erythroblastosis Fetalis" in "Blood Group Disorders In Pregnancy", Ch. 7, p. 103).

At the present time, anti-Rh(D) antibody for use in both Rh-typing of RBCs and passive immunisation of Rh(D−) mothers is largely obtained directly from female donors immunised during pregnancy or from immunised male volunteers. The success of the programme of post-partum prophylactic administration of human anti-Rh(D) immunoglobulin to Rh(D−) women has, however, resulted in a dramatic reduction in the number of naturally alloimmunised women (Urbantak, S. J., "RhD haemolytic disease of the newborn: the changing scene", Br. Med. J. (1985) 291, 4–6). Also, deliberate immunisation of individuals with Rh(D+) RBCs carries the risks common to receiving any transfusion of RBCs, e.g. risk of transmission of hepatitis viruses and HIV. Hence, there is much interest in obtaining human monoclonal anti-Rh(D) antibodies for both diagnostic and therapeutic purposes.

As state above, in routine blood testing, blood types are divided into Rh(D+) and Rh(D−) on the basis of the apparent presence or absence of Rh(D) antigen on the RBCs as indicated by agglutination tests with anti-Rh(D). However, a small number of persons with apparently Rh(D−) blood have RBCs that are not directly agglutinated by anti-Rh(D) during such routine testing, but that do react when the D-typing test is performed using selected anti-Rh(D) reagents by the indirect antiglobulin test. Cells thus identified are designated $D^u$. The frequency of the $D^u$ phenotype is about 0.2% overall, 0.6% among Caucasians, and about 1.5% of all Rh(D−) gravid women. At least three different mechanisms may be responsible for the expression of the $D^u$ phenotype: (1) hereditary absence of a portion of the complete Rh(D) antigen, (2) gene interaction with suppression of D by C in the trans position, and (3) a D gene producing a weak antigen.

In the early 1950s, reports first appeared of the presence of anti-Rh(D) in individuals of the $D^u$ phenotype following blood transfusion with Rh(D+) blood or pregnancy resulting in the birth of a Rh(D+) infant. It later became apparent that in some individuals whose blood is classified Rh(D+) parts of the Rh(D) antigen are missing from the RBCs. When exposed by transfusion or pregnancy to Rh(D+) RBCs carrying the complete Rh(D) antigen, persons carrying an incomplete Rh(D) antigen on their RBCs are capable of making alloanti-D against the Rh(D) antigen portion they lack. The blood of such individuals is called D variant when the RBCs react directly with routine anti-Rh(D) reagents or $D^u$ variant when the cells react only by the indirect antiglobulin technique.

The observation that allo anti-Rh(D) can be produced in patients who have Rh(D+) RBCs has led to common usage of the term "D mosaic" to describe the Rh(D) antigen in its complete native form. Routine anti-Rh(D) reagents generally cannot differentiate those RBCs that lack part of the D mosaic from those that have all the D components.

The D variant phenotypes have been categorised by Tippert and Sanger (Vox. Sang. (1962)7, 9–13). This system is based on the interaction of RBCs and serum from D– and $D^u$ variant individuals. The six categories (see Table II below) allow for expansion; subdivisions are already recognised in categories III, IV and V. Categories I and II have been found to have so many similarities that they are now generally considered as a single sub-group.

TABLE II

Tippett and Sanger categories for D– or $D^u$ positive blood with anti-Rh (D)

| Category | Racial origin | Usual haplotype |
| --- | --- | --- |
| I | White | DCe |
| II | | |
| IIIa | Black | |
| IIIb | Usually Black | Dce |
| IIIc | White | |
| IVa | Mostly Black, some White | |
| IVb | White | Dce |
| Va | Black and White | |
| Vb | White | $D^u$ce |
| Vc | Black and White | |
| VI | Nearly all White | $D^u$Ce |

An alternative, but lesser used, classification by Wiener uses letters A,B,C,D instead of Roman Numerals. Although there is no direct correlation between the two systems, it is often considered that $D^B$ and $D^{VI}$ are interchangeable.

Although the frequency of D and $D^u$ variant individuals within the human population is relatively low, the total number of individuals of these blood types who potentially have some risk of effective anti-Rh(D) formation as a result of exposure by blood transfusion or pregnancy to non-variant Rh(D+) cells is far from insignificant. Moreover, in addition to Rh(D–) women who give birth to Rh(D+) or $D^u$ infants, $D^u$ variant women who give birth to an Rh(D+) infant may also benefit from post-partum anti-Rh(D) treatment to reduce the risk of HDN (White, C. A. et al. (1983) Am. J. Obstet. Gynecol. 145, 1069–1073). Anti-sera capable of distinguishing D and $D^u$ variant RBCs are not widely available. Hence, provision of anti-Rh(D) monoclonal antibodies with a range of binding specificities for D and $D^u$ variant RBCs is seen as useful in enabling the more ready identification and categorisation of individuals possessing such cells (especially D or $D^u$ variant pregnant females who are suitable candidates for prophylactic anti-Rh(D) treatment) as well as for providing further structural information on the Rh(D) antigen complex.

Human monoclonal anti-Rh(D) antibody production has previously been achieved by:

(a) directly cloning Epstein Barr virus transformed B lymphocyte cell lines (hereinafter referred to as EBV-transformed LCL) derived from B lymphocytes of anti-Rh(D) positive donors (see GB-A 2127434; Crawford et al. (1983) Lancet 1, 386–388 and Paire et al (1986) Immunol. Lett. 13, 137–141), (b) cloning hybridoma cell lines formed by fusing anti-Rh (D) producing, EBV-transformed LCL with mouse, mouse-human or human myeloma cell lines (see copending British application no. 8709748, Thompson et al. (1986) Immunol. 58, 157–160 and EP-A-0162918), or (c) by fusion of a human LCL with immune B cells (Lowe et al (1986) Vox. Sang. 51, 212–216).

Figure 1:
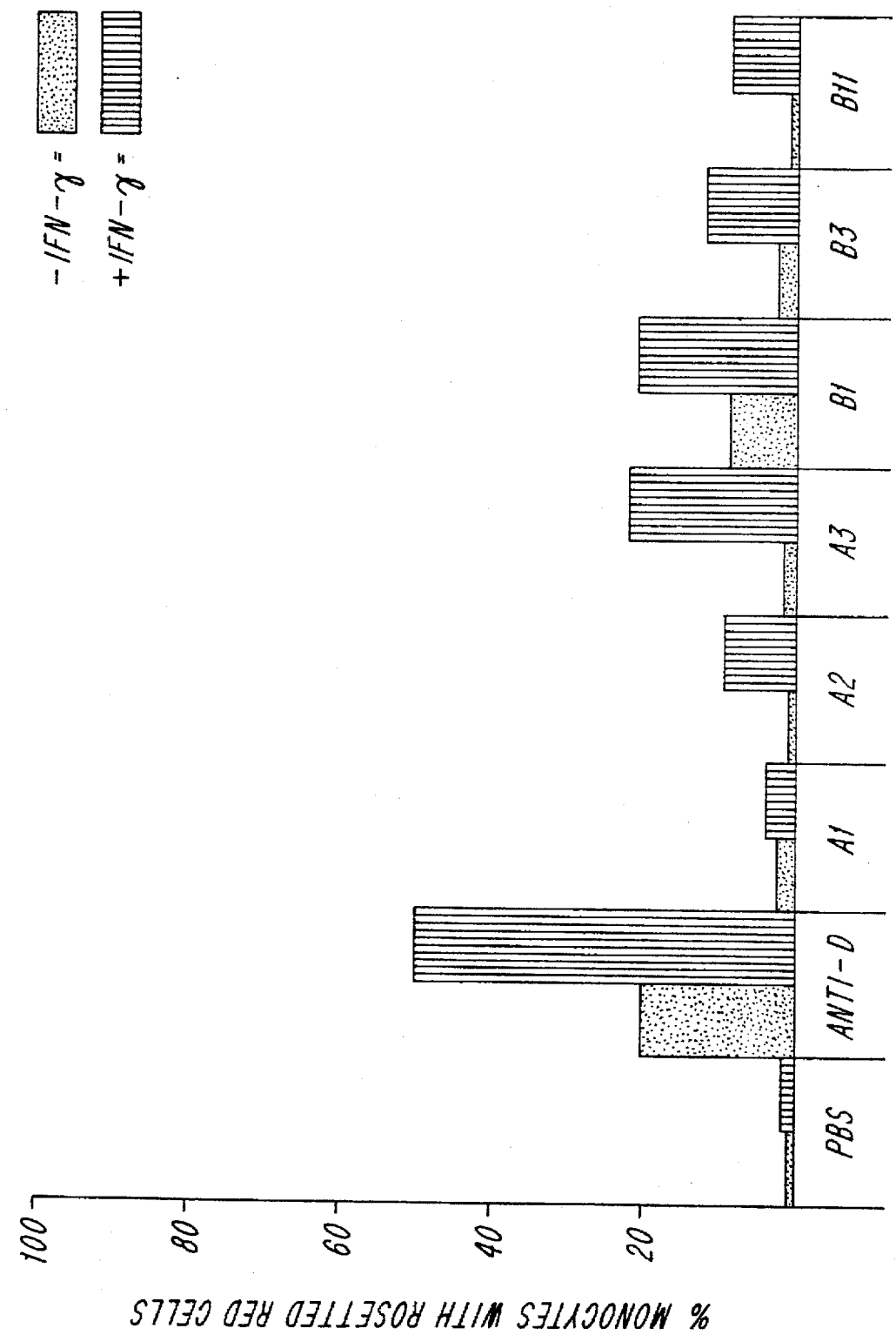
FIG. 1 is a comparison of phagocytosis results (expressed as the percentage of monocytes with one or more adherent or phagocytosed red cells) obtained with culture supernatants of clones A1, A2, A3, B1, B3 and B11 and a conventional polyclonal anti-Rh(D) serum.

By cloning EBV-transformed LCL from 3 anti-Rh(D) positive donors, we have been able to obtain, however, monoclonal anti-Rh(D) antibodies of the IgG class which have a particularly useful binding specificity spectrum not shown for any previously disclosed anti-Rh(D) monoclonal antibody reagent.

According to the present invention, we provide human monoclonal antibodies having the following essential characteristics:

(a) exhibiting activity against Rh(D) antigen, but not C, c, E or e antigens of the Rh blood group system;

(b) being IgG1 proteins;

(c) having kappa light chains;

(d) being G1m (3) or G1m (1, 17) allotype;

(e) exhibiting activity against $D^u$ cells by an indirect antiglobulin test;

(f) exhibiting activity against $D^{IV}$, $D^V$ and $D^{Tar}$ ($D^{VII}$) variant antigens; and (g) being inactive against $D^{VI}$ or $D^B$ variant antigens, and antigen-binding fragments thereof.

Such monoclonal antibodies can be employed as routine anti-Rh(D) reagents to classify RBCs as Rh(D+), $D^u$ or Rh(D–).

For this purpose, a monoclonal antibody of the present invention may be employed either alone or in combination with one or more further anti-Rh(D) antibodies, preferably monoclonal antibodies having one or more additional binding specificities. Thus, for example, a monoclonal antibody of the present invention may be advantageously blended with a further monoclonal antibody capable of binding the $D^{VI}$ variant to provide an anti-Rh(D) reagent of broader specificity capable of classifying $D^{VI}$ variant RBCs as D-positive. In such an anti-Rh(D) reagent, an IgG1 antibody of the present invention may, for example, be combined with an IgG1 monoclonal antibody of the type disclosed in our co-pending International application of even date herewith claiming priority from GB-A 8722020, having the following binding characteristics:

(a) exhibiting activity against Rh(D) antigen, but not C, c, E or e antigens of the Rh blood group system;

(b) exhibiting activity against $D^V$ $D^{Tar}D(^{VII})$ $D^{VI}$ and $D^B$ variant antigens; and (c) being substantially non-reactive with non-papain treated $D^{IV}$ cells in an IAG test.

Amongst such antibodies, particularly preferred for use in combination with an anti-Rh(D) monoclonal antibody of the present invention is the monoclonal antibody designated B7 deposited at the European Collection of Animal Cell Cultures Public Health Laboratory Service Center for Applied Microbiology and Research, Porton Down, Salisbury, Wiltshire SP4 OJG, England under accession No. ECACC 87091603 on 16th Sep. 1987.

If monoclonal antibodies of the present invention are used for Rh-typing in parallel with an anti-Rh(D) reactive against the $D^{VI}$ variant, e.g. an appropriate polyclonal anti-Rh(D) serum, those blood samples giving a positive result in an agglutination test with the latter, but negative results with a monoclonal antibody of the invention can be predicted to be mainly or entirely of the $D^{VI}$ category (since this is virtually the only D variant antigen against which the new monoclonal antibodies are inactive). It has been established that amongst individuals classified as Rh(D+) or $D^u$ by a conventional agglutination test, but who are capable of making anti-Rh(D), a high percentage have the $D^{VI}$ variant antigen (Mollison, P. L. (1983) in "Blood Transfusion In Clinical Medicine", Ch. 8, p 330). One use of the monoclonal antibodies of the invention is, indeed, in investigating the incidence of individuals of the $D^{VI}$ type in the population.

A monoclonal antibody of the present invention may also be of particular value for use in an anti-Rh(D) typing reagent to supplement the specificity of an anti-Rh(D) with no or only weak anti-$D^u$ activity, i.e. insufficient activity against $D^u$ cells to be able to reliably distinguish such cells from D-negative cells in a conventional agglutination test. Indeed, under FDA regulations in the U.S.A. governing commercial anti-Rh(D) typing reagents, it is obligatory for such a reagent to be able to distinguish $D^u$ RBCs from truly D-negative RBCs. Especially preferred amongst combination anti-Rh(D) reagents of the present invention are such reagents satisfying the above condition wherein an IgG anti-Rh(D) of the invention is employed together with an IgM anti-Rh(D) with only weak $D^u$ activity, e.g. an IgM monoclonal anti-Rh(D) selected from the monoclonal IgMs of the deposited hybridoma cell lines MAD-2 (cell line 866041803, deposited on Apr. 18, 1986 at the European Collection of Animal Cell Culture, Public Health Laboratory Service Center for Applied Microbiology and Research, Porton Down, Salisbury, Wiltshire SP4 OJG, England) and FOM-1 (cell line 87021301, deposited on Feb. 13, 1987 at the European Collection of Animal Cell Culture, Public Health Laboratory Service Center for Applied Microbiology and Research, Porton Down, Salisbury, Wiltshire SP4 OJG, England), which form inter alia, the subject matter of published European Patent Application 0251440. Such a reagent will advantageously be further complemented with at least one further IgG monoclonal anti-Rh antibody which individually exhibits activity with $D^u$ red cells by the indirect antiglobulin test, such that the blended reagent reacts by the same test with $D^u$, $D^{IV}$, $D^V$ and $D^{VI}$ cells. When Rh typing is carried out with such a reagent, D-positive cells will firstly be directly agglutinated by the IgM anti-Rh(D). The remaining non-agglutinated cells (apparently D-negative) may then be subsequently divided into truly D-negative and $D^u$ cells by addition of conventional Coomb's reagent for an indirect antiglobulin test, whereupon $D^u$ cells binding antibody will be agglutinated and thus distinguished.

The monoclonal anti-Rh(D) antibodies of the invention can be made by conventional methods known for the production of monoclonal antibodies and in particular by the culture of EBV-transformed human B-lymphocytes selected on the basis of secretion of anti-Rh(D) immunoglobulin having the characteristics set out above for the required antibodies. The culture supernatants so produced constitute a further feature of the present invention.

We have now investigated in detail 9 cloned EBV-transformed LCL which produce $IgG_1$ anti-Rh(D) monoclonal antibodies as defined above. All these cloned cell lines were obtained by starting with peripheral B lymphocytes from 2 chosen anti-Rh(D) donors and employing the procedure described in GB-A 2145113 or a substantially similar procedure to establish and clone EBV-transformed LCL producing a monoclonal antibody of the desired specificity (see Example 1). In continuous culture using RPMI-1640 medium supplemented with 10% (v/v) mycoplasma free-fetal calf serum, 0.2 mg/ml arginine and antibiotics to prevent mycoplasma growth, they have been found to be highly stable and to provide a culture supernatant having an anti-Rh(D) titre, as determined by an indirect antiglobulin (IAG) assay in low ionic strength saline versus $R_1R_1$ (CDe/CDe) RBCs, in the range 2000–8000. Such a culture supernatant is suitable for use in Rh-typing without the need for concentration and indeed may be diluted for use. Four of the selected cell lines (A1, A2 and A3 derived from a donor A) have been shown to maintain a stable anti-Rh(D) titre in continuous culture for over 2 years. Four further cell lines capable of providing a culture supernatant as above (B1, B2, B3 and B11 derived from a donor B) have been maintained in continuous culture for over 8 months without substantial decrease of anti-Rh(D) titre. Antibody production characteristics of the above-mentioned specific clones in continuous culture are summarised in Tables IIIa and IIIb below.

TABLE IIIa

| IAG titre (3% RBCs in low ionic strength saline) | |
| --- | --- |
| $R_1r$ cells | 64–512 |
| $R_1R_1$ cells | 2000–8000 |
| $R_1"r$ cells | 8–512 |
| Microtitre with bromelain-treated $R_1R_2$ cells | 33,000–131,000 |
| Anti-Rh(D) (IU/ml) | 10–98 |
| IgG (μg/ml) | 3.9–11.0 |

TABLE IIIb

| Supernatant culture | IAG reactivity of supernatant with 3% RBCs in low ionic strength saline. (Grade: 0 to 6) | | | | | | | | |
| --- | --- | --- | --- | --- | --- | --- | --- | --- | --- |
| | A1 | A2 | A3 | B1 | B2 | B3 | B11 | B12 | B13 |
| RBC phenotype | | | | | | | | | |
| $R_1R_1$ | 6 | 6 | 6 | 6 | 6 | 6 | 6 | 6 | 6 |
| $R_1u_r$ | 6 | 6 | 6 | 6 | 6 | 4 | 5 | 6 | 6 |
| $R_o"r$ | 6 | 6 | 6 | 6 | 6 | 6 | 6 | 6 | 6 |

It was further found that those monoclonal antibodies of the invention that were tested reacted by IAG with RBCs of phenotypes $R_2rG-$, $hr^s-$, $R_1R_z$ and $R_2R_z$ but are negative with r"Gr, $r^m$, $r^G$, $r'^s r$, $hr^B-$, $r'^w r$ and Rh33+.

Gm allotyping of the antibodies of clones A1, A2, A3, B1, B2, B3, B11, B12 and B13 has shown that they fall into two allotype groups. Using the W.H.O. (1974) notation, the IgG1 anti-Rh(D) antibodies of clones A1, A2 and A3 were found to be of the Glm (1, 17) allotype, whereas the antibodies of the remaining above-mentioned clones derived from donor B were found to be of the allotype Glm(3). The latter antibodies are of particular interest from the point of view of providing a monoclonal antibody preparation for use in post-partum immunisation of Rh(D−) mothers. In general, the antibodies in the Glm (1, 17) allotype group were active against the $\overline{R^N}$ antigen, whereas those of Glm(3) allotype were not.

IgG1 anti-RbD antibodies are generally poor promoters of phagocytosis of Rh(D+) RBCs by monocytes and macrophases. However, we have found that-IgG1 anti-Rh(D) antibodies of the Glm(3) allotype, e.g. the IgG1 antibodies of clones B1, B2, B3, B11, B12 and B13, unlike IgG1 anti-Rh(D) antibodies of the Glm(1, 17) allotype, are highly effective in mediating lysis of sensitised RBCs by K lymphocytes in an antibody-directed cell cytoxicity (ADCC) assay. This is in keeping with the previously reported observation of Parinaud et al. that foetal haemolysis is more severe with maternal IgG1 antibodies of the Glm(4) allotype, i.e. Glm(3) allotype according to the W.H.O (1974) nomenclature (Am. J. Obstet. Gynecol (1985) 1111–1115).

Thus, according to a further aspect of the present invention, we provide a monoclonal IgG1 antibody of the present invention, preferably a monoclonal antibody of the present invention having the allotype Glm(3), for use in passive immunisation of an Rh(D−) or D− or $D^u$− variant mother after the birth of an Rh(D+) child to prevent sensitisation of the mother to Rh(D) antigen. A sterile solution of such an antibody for human injection may be formulated in any physiologically acceptable aqueous medium, for example isotonic phosphate buffered saline or serum. Alternatively, the antibody may be supplied in a freeze-dried formulation ready for reconstitution prior to use. To provide a highly efficient prophylactic preparation for use in the prevention of HDN, a monoclonal anti-Rh(D) of the present invention, especially such an antibody of the Glm(3) allotype, may desirably be employed with one or more further anti-Rh(D) antibodies, for example one or more further anti-Rh(D) antibodies promoting phagocytosis of Rh(D+) RBCs in vivo, e.g. an anti-Rh(D) monoclonal antibody of the IgG3 sub-class, such as an IgG3 monoclonal anti-Rh(D) of our co-pending International Application No. PCT/GB88/00756 (WO89/02600) filed Sep. 16, 1988, claiming priority from GB-A 8722019, the contents of which are incorporated herein by reference. The aforementioned IgG3 monoclonal anti-Rh(D) antibodies are exemplified by the monoclonal antibody of the deposited cell line ECACC (cell line 87091601, deposited on Sep. 16, 1987 at the European Collection of Animal Cell Culture, Public Health Laboratory Service Center for Applied Microbiology and Research, Porton Down, Salisbury, Wiltshire SP4 OJG, England). For routine use, ideally a prophylactic pharmaceutical composition of the present invention will include an anti-$D^{VI}$ antibody.

According to a still further aspect of the present invention, we provide a method of Rh-typing of RBCs wherein an aqueous solution of a monoclonal anti-Rh(D) immunoglobulin of the present invention is employed. The monoclonal immunoglobulin is preferably contained in a culture supernatant which may be used directly or, more usually, after dilution. Particularly preferred for use in Rh-typing are culture supernatants containing monoclonal anti-Rh(D) immunoglobulin according to the present invention which will agglutinate at high dilution (e.g. 1:1000 dilution) enzyme-treated RBCs carrying the Rh(D) antigen and in the IAG test will agglutinate $D^u$ RBCs at, for example, 1:10 dilution.

As hereinbefore indicated, it may be desirable to blend an IgG1 antibody of the present invention with one or more further anti-Rh(D) monoclonal antibodies of different specificity, e.g. a further IgG1 antibody having anti-$D^{VI}$ activity. Suitable diluents include physiological saline or phosphate buffered saline, advantageously containing bovine serum albumin and a surfactant or suspending agent such as Tween 80 or methyl cellulose.

The cell lines A3 and B2 were deposited on 16th Sep. 1987 at the European Collection or Animal Cell Cultures, Porton Down, Salisbury, Wiltshire SP4 OJG, England under accession numbers ECACC (cell line 87091605, deposited on Sep. 16, 1987 at the European Collection of Animal Cell Culture, Public Health Laboratory Service Center for Applied Microbiology and Research, Porton Down, Salisbury, Wiltshire SP4 OJG, England) and ECACC (cell line 87091604, deposited on Sep. 16, 1987 at the European Collection of Animal Cell Culture, Public Health Laboratory Service Center for Applied Microbiology and Research, Porton Down, Salisbury, Wiltshire SP4 OJG, England) respectively.

Further details of the preparation of the above noted deposited cell lines of the present invention and the identifying characteristics of the culture supernatants obtainable by continuous culture of these are provided in Example 1 of the following non-limiting examples.

EXAMPLE 1

(i) Establishment and Cloning of Anti-Rh(D) Producing EBV-transformed LCL (a) Sources of B Lymphocytes Donor A: female, immunised during her first and only pregnancy (which resulted in delivery of a normal Rh(D+) infants), boosted with 0.5 ml packed Rh(D+) ($R_2r$) RBCs 4 years after parturition, and a peripheral blood sample obtained 8 days after boosting when her serum anti-D level was 60 IU/ml. Donor B: male, initially immunised by transfusion in 1966, boosted 6 times since and last boosted 13 days before donating a "buffy coat" fraction (white cells) in 1985 when his serum anti-D level was 318 IU/ml.

(b) Establishment of cell lines

Peripheral blood mononuclear cells from donor B were separated on Lymphoprep (Nyegaard and Co), incubated in the presence of EBV (1 ml culture supernatant from filtered mycoplasma free B95-8 cell line per $10^7$ cells) at 37° C. for 1 hour and washed in phosphate-buffered saline (PBS). Aliquots were either (a) plated at $0.5 \times 10^6$ cells/ml in 2 ml wells using lymphoblastoid cell culture medium (RPMI-1640 medium containing 10% (v/v) mycoplasma free foetal calf serum (FCS), 8.2 mg/ml arginine, 100 IU/ml penicillin (Glaxo), 50 μg/ml streptomycin (Glaxo), 25 IU/ml polymixin (Glaxo), 25 μg/ml kanamycin (Gibco), 20 μl/ml fungizone (Squibb), 25 μg/ml gentamycin sulphate (Sigma) and 20 μg/ml trobicin (UpJohn)), supplemented with either 1% (v/v) phytohaemagglutinin (PHA) or 0.5 μg/ml cyclosporin A (CsA); or (b) enriched for surface anti-D positive lymphocytes by rosetting with bromelain-treated $OR_1R_2$ (CDe/cDE) RBCs prior to plating out as above.

Four cell lines from donor B were set up: LCL and enriched LCL with either initial PHA or CsA supplementation.

Isolated peripheral blood mononuclear cells from donor A were similarly infected With EBV. After washing with PBS, the cells were resuspended in lymphoblastoid cell culture medium supplemented with 1% (v/v) PHA and dispensed into 2 ml wells above a feeder layer of mouse peritoneal macrophages.

All the cultures were subsequently incubated at 37° C. in 5% $CO_2$, 95% humidified air. Medium changes were performed every 3 to 4 days and, after 3 weeks culture, the cells were transferred to 50 ml flasks. All the cell lines (except that giving rise to clone B3) were enriched by rosetting at 3–4 weekly intervals.

(c) Cloning

Cells were plated out at limiting dilution at 5 and 10 cells per well in flat bottomed 96-well plates over a feeder layer of mouse peritoneal macrophages (Doyle et al. (1985) Human Immunology 13, 199–209). Cultures were fed once a week and after 3–4 weeks cloned cells positive for anti-D were grown up.

(d) Derivation of clones

Three clones producing anti-Rh(D) antibody of the IgG1 sub-class (designated A1, A2 and A3) were derived from B lymphocytes of donor A. The polyclonal cell line giving rise to these clones was initiated with PHA and sequentially enriched for anti-Rh(D) positive cell by rosetting 13 times before cloning.

Five further clones producing anti-Rh(D) antibody of the IgG1 sub-class (designated $B_1$, $B_2$, $B_3$, B11 and B12) were derived from B lymphocytes of donor B via a polyclonal cell line initiated with PHA. B1 and B2 were derived from cell lines repeatedly (6×) selected by rosetting after establishing an LCL. B11 and B12 were derived from a cell line rosetted only twice and B3 was produced from an LCL maintained for 1 year without rosetting before cloning. [It should be noted that B11 was erroneously designated C1 in the priority application (GB-A 8722018)].

A further anti-Rh(D) IgG1 producing clone (B13) was derived via a donor B polyclonal cell line supplemented with CsA. This cell line was established from lymphocytes selected for anti-Rh(D) immediately after transformation by EBV and was subsequently re-rosetted four times.

The results of tissue type and karotype analysis of the above selected cell lines are set out in Table IV below.

TABLE IV

| Cell Line | A1 A2 A3 | B1 B2 B3 B11 B12 B13 |
|---|---|---|
| Donor | A | B |
| Sex | Female | Male |
| Tissue Type | | |
| HLA: A | 2,w19 | 1,3 |
| B | 44,35 | 8,35 |
| DR | 315 | 1,3 |
| Karotype | | |
| sex chromosomes | xx | xy |
| ploidy | most cells diploid | most cells diploid |

(e) Quantitation of anti-Rh(D) activity and IgG in culture supernatants

Anti-Rh(D) activity in the supernatants was quantified against British national standards by Auto Analyser. The mean of at least two determinations was calculated. The quantitative estimation of IgG was performed by ELISA (modification of the method of Wakefield et al. in Clin. Chim. Acta. (1982) 123, 303–310) with at least eight determinations for each supernatant. Coating antibody (affinity purified goat anti-human IgG (Sigma)) was used at 1/200 in 0.05M carbonate buffer pH 9.6. Supernatants and standard (purified human IgG (Sigma)) were diluted in RPMI 1640+ 10% FCS. Peroxidase-conjugated goat anti-human IgG (Sigma) was diluted 1/500 in PBS+0.05% Tween 20 and the substrate was TMB (3,3', 5,5'-tetramethyl benzidine).

Not all the cell lines established under different experimental conditions showed stable antibody production. However, all the cell lines which were subsequently cloned had maintained high titres (over 1/33,000 by microtitre) of anti-D for over 6 months. All clones from these cell lines were positive for anti-D and maintained their titres throughout the duration of continuous culture (A1, A2 and A3—over 2 years; B1, B2, B3 and B11—over 8 months). The doubling time was 3–7 days. The cells grew well in suspension culture with no loss of antibody production.

(f) Immunoglobulin class and subclass determination

An immunodot assay (McDougal et al. (1983) J. Imm. Meth. 63, 281–290) was used to determine the reaction of the monoclonal anti-Rh(D) antibodies absorbed to nitrocellulose with anti-IgG, anti-IgM, anti-kappa and anti-lambda antiserum (Serotec); positive reactions were detected with peroxidase-conjugated anti-sheep IgG (Serotec) followed by colour development with 4-chloro-1-naphthol. The IgG subclass was evaluated by agglutination of anti-D coated RBCs by monoclonal anti-subclass antibodies (Unipath).

The presence of single discrete bands for antibody derived from the selected cell lines after SDS-polyacrylamide gel electrophoresis was evidence of monoclonality.

(g) SDS-Page and Western Blotting.

Iscove's supernatants (serum free) were electrophoresed under reducing conditions on 15% polyacrylamide gels (Laemmli, Nature (1970) 227, 680–685). The separated proteins were then electrophoretically transferred to nitrocellulose membranes (Brunette, Annals Biochem. (1981) 112, 195–203), which were probed with anti-IgG antiserum (Serotec) and detected as above. P(h) Protein A absorption 2 ml volumes of supernatants were run twice down a 25 mm (1 ml) column of Protein A Sepharose Cl-4B (Sigma) and absorption of anti-Rh(D) assessed by titration.

(i) Gm allotyping

RBCs were coated with the monoclonal anti-D antibodies and agglutination assessed using panels of Gm allotyping reagents (Birmingham or Amsterdam).

The Gm allotypes of the monoclonal antibodies of clones A1, A2, A3, B1, B2, B3, B11, B12 and B13 together with other characteristics are given in Table V below.

TABLE V

Identification of immunoglobulin class, subclass, and Gm allotype

| Monoclonal antibody: | A1 | A2 | A3 | B1 | B2 | B3 | B11 | B12 | B13 |
|---|---|---|---|---|---|---|---|---|---|
| Anti-IgG: | +++ | +++ | +++ | +++ | +++ | +++ | +++ | +++ | +++ |
| anti-IgM: | − | − | − | − | − | − | − | − | − |
| anti-kappa: | +++ | +++ | +++ | +++ | +++ | +++ | +++ | +++ | +++ |
| anti-lambda: | − | − | − | − | − | − | − | − | − |
| Anti-IgG1: | 6 | 6 | 6 | 6 | 6 | 6 | 6 | 6 | 6 |
| anti-IgG2: | 0 | 0 | 0 | 0 | 0 | 0 | 0 | 0 | 0 |
| anti-IgG3: | 0 | 0 | 0 | 0 | 0 | 0 | 0 | 0 | 0 |
| anti-IgG4: | 0 | 0 | 0 | 0 | 0 | 0 | 0 | 0 | 0 |
| Heavy chain $M_r$ (kDa): | 55.5 | 55 | 55 | 54 | 54 | 54 | 55 | * | * |
| Protein A absorption | +++ | +++ | +++ | +++ | +++ | +++ | +++ | +++ | +++ |

TABLE V-continued

Identification of immunoglobulin class, subclass, and Gm allotype

| Monoclonal antibody: | A1 | A2 | A3 | B1 | B2 | B3 | B11 | B12 | B13 |
|---|---|---|---|---|---|---|---|---|---|
| Gm allotype: | G1 m(1,17) Km − 1 | G1 m(1,17) Km − 1 | G1 m(1,17) Km − 1 | G1 m(3) Km − 1 | G1 m(3) Km − 1 | G1 m(3) Km − 1 | G1 m(3) Km − 1 | G1 m(3) Km − 1 | G1 m(3) Km − 1 |

*not determined (ii) Serology

Anti-D titration was performed by adding 50 µl of 0.1% suspension of bromelain-treated $OR_1R_2$ (CDe/cDE) erythrocytes to 50 µl of supernatant, neat and serially diluted two-fold, in V-well microplates. After incubation at 37° C. for 60 mins, and centrifugation at 600 rpm for 3 mins, they were read macroscopically by tilting the plate at 70° and allowing negative reactions to trail. The degree of agglutination was graded in conventional manner and the titres given as the highest dilution giving complete agglutination (see Table IIIa). Anti-D titres were also determined by the IAG test using rabbit anti-human IgG and 3% $R_1r$, $R_1R_1$, $R_1^ur$ or $R_o^ur$ cells in low ionic strength saline (LISS). The anti-D activity of the monoclonals against a panel of D variant red cells was also assessed using saline, albumin, papain and IAG (in LISS) tests. In a separate series of tests, the reactivity of the monoclonal anti-Ds of $A_1$, A2, A3, B1, B3 and B11 with $D^u$ red cells (15 sets of $R_1^ur$ cells and 10 sets of $R_2^ur$ cells, each set being taken from a different individual) was assessed by IAG (in LISS) using untreated supernatants. Using the same procedure, culture supernatant of B1 was further compared with culture supernatant of B2 against 1 set of $R_1^ur$ cells and 3 sets of $R_o^ur$ cells. The supernatants were tested on a Technicon Autogrouper 16C at dilutions ranging between 1:5 to 1:10,000.

Tests against cells of "normal" RhD positive or RhD negative phenotypes by albumin, papain and indirect antiglobulin techniques revealed that all the IqG1 monoclonal antibodies showed specificity for the D antigen (see Table VI below). None of the monoclonal anti-Ds were reactive-by saline. When tested by IAG against "partial" D positive cells, the antibodies agglutinated $D^{IV}$ $D^V$ and $D^{Tar}(D^{VII})$ red cells, but not $D^{VI}$ or $D^B$ (see Table VII below). As shown in Table VIII, the supernatants of A1, A2, A3, B1, B3 and B11 were all found to show stronger reactivity by IAG tests with 25 $D^u$ cells (i.e. weak D) than polyclonal antiserum (the routine reagent employed by the South Western Regional Transfusion Service in the U.K). Using the same IAG test procedure, culture supernatant of B1 was found to exhibit similar or identical reactivity to culture supernatant of B2 against 4 further sets of $D^u$ cells (see Table IX). All the IgG1 monoclonal antibodies reacted more strongly with $R_1r$ ( CDe/cde) or $R_1R_1$ (CDe/CDe) cells than with either $D^u$ or $D^V$ cells, though there were some differences in titres between the supernatants. When tested separately on a Technicon Autogrouper 16C, supernatants of A2, B1 and B11 could be used diluted to 1:1,000 for use as a routine anti-D and at 1:10 dilution to distinguish $D^u$ from D negative cells.

TABLE VI

Serology of monoclonal anti-Rh (D) antibodies

| RBC phenotype | $R_1R_1$ | $R_2R_2$ | $R_or$ | r'r | r"r | rr |
|---|---|---|---|---|---|---|
| Saline 37° C.: | 0 | 0 | 0 | 0 | 0 | 0 |
| Albumin 37° C.: | 4–5 | 4–5 | 4–5 | 0 | 0 | 0 |
| Papain 37° C.: | 5 | 5 | 5 | 0 | 0 | 0 |
| IAG: | 5 | 5 | 5 | 0 | 0 | 0 |

(Grade: 0 to 5)

TABLE VII

Reaction of monoclonal anti-Rh (D) antibodies with "partial" D positive RBCs by IAG

| Monoclonal antibody: | A1 | A2 | A3 | B1 | B2 | B3 | B11 |
|---|---|---|---|---|---|---|---|
| $D^{IV}$: (n = 1) | 5 | 5 | 5 | 5 | 4 | 3 | 5 |
| $D^V$: (n = 3) | 5 | 5 | 5 | 5 | 5 | 5 | 5 |
| $D^{Tar}(D^{VII})$: (n = 3) | 5 | 5 | 5 | 5 | 5 | 5 | 5 |
| $D^{VI}$: (n = 3) | 0 | 0 | 0 | 0 | 0 | 0 | 0 |
| $D^B$: (n = 5) | 0 | 0 | 0 | 0 | 0 | 0 | 0 |

(Grade: 0 to 5)

TABLE VIII

Reactivity of monoclonal and polyclonal anti-Ds with $D^u$ RBCs by IAG (15 $R_1^ur$ and 10 $R_2^ur$)

| Monoclonal antibody: | A1 | A2 | A3 | B1 | B3 | B11 | Polyclonal anti-Rh (D) Serum |
|---|---|---|---|---|---|---|---|
| Number with | | | | | | | |
| Grade 6: | 16 | 15 | 11 | 6 | 1 | 5 | 0 |
| Grade 5: | 8 | 9 | 12 | 16 | 7 | 17 | 4 |
| Grade 4: | 1 | 1 | 2 | 3 | 9 | 3 | 12 |
| Grade 3: | 0 | 0 | 0 | 0 | 4 | 0 | 7 |
| Grade 2: | 0 | 0 | 0 | 0 | 4 | 0 | 1 |
| Grade 1: | 0 | 0 | 0 | 0 | 0 | 0 | 1 |

TABLE IX

| Monoclonal antibody | B1 | B2 (titres by IAG) |
|---|---|---|
| RBCs | | |
| $R_1^ur$ | 512 | 512 |
| $R_o^ur$ | 32 | 16 |

TABLE IX-continued

| Monoclonal antibody | B1 | B2 (titres by IAG) |
|---|---|---|
| $R_o^a r$ | 512 | 512 |
| $R_o^a r$ | 512 | 512 |

(iii) Lymphocyte ADCC assay

Equal volumes (50 μl) of target cells (chromium-51 labelled $R_1R_1$ RBC suspension), effector cells (K lymphocytes) and anti-D culture supernatant were incubated overnight at 37° C. in microplates after mild centrifugation, and the chromium-51 release measured (Urbantak (1979) Br. J. Haematol. 42, 303–314). The effector:target cell ratio was 15:1.

The culture supernatants of clones B1, B2, B3, B11, B12 and B13 containing a monoclonal anti-Rh(D) of the Glm(3) allotype, unlike the other culture supernatants with antibody of the Glm(1,17) allotype, were found to be highly active in mediating lysis of sensitised RBCs in the presence of K cells see Table X below).

TABLE X

| Monoclonal antibody: | A1 | A2 | A3 | B1 | B2 | B3 | B11 | B12 | B13 | Anti-Rh (D) serum |
|---|---|---|---|---|---|---|---|---|---|---|
| % specific lysis: | | | | | | | | | | |
| Effector KF | -2 | -1 | -2 | 91 | * | 99 | 83 | * | * | 95 |
| Effector KL | * | 13 | * | * | 78 | * | * | * | * | * |
| Effector BW | 5 | 4 | 3 | 56 | * | 73 | 70 | * | * | 92 |
| Effector BK | 4 | 15 | * | 91 | * | * | 81 | 71 | 75 | * |

*not determined (iv) U937 Monocyte rosetting and phagocytosis assay

100 μl packed $OR_1R_2$ RBCs were sensitised with 500 ul anti-Rh(D) (previously adjusted to 1 ug/ml) at 37° for 60 minutes, washed and resuspended at $1 \times 10^8$ cells/ml in RPMI. U937 cells were taken in the log phase of growth and cultured for two days either in the presence or absence of interferon-γ (Amersham) at 50 U/ml. $45 \times 10^6$ RBCs were then added to a pellet of $1.5 \times 10^6$ U937 cells and mixed, giving a ratio of 30:1. For the rosetting assay, the cells were incubated at room temperature for 5 minutes, spun at 600 rpm for 3 minutes and examined in a haemocytometer after a further 5–20 minutes. Phagocytosts was assessed immediately after incubating the cells at 37° for 3 hours. Results were expressed as the percentage of monocytes with one or more adherent or phagocytosed RBCs.

Figure 2:
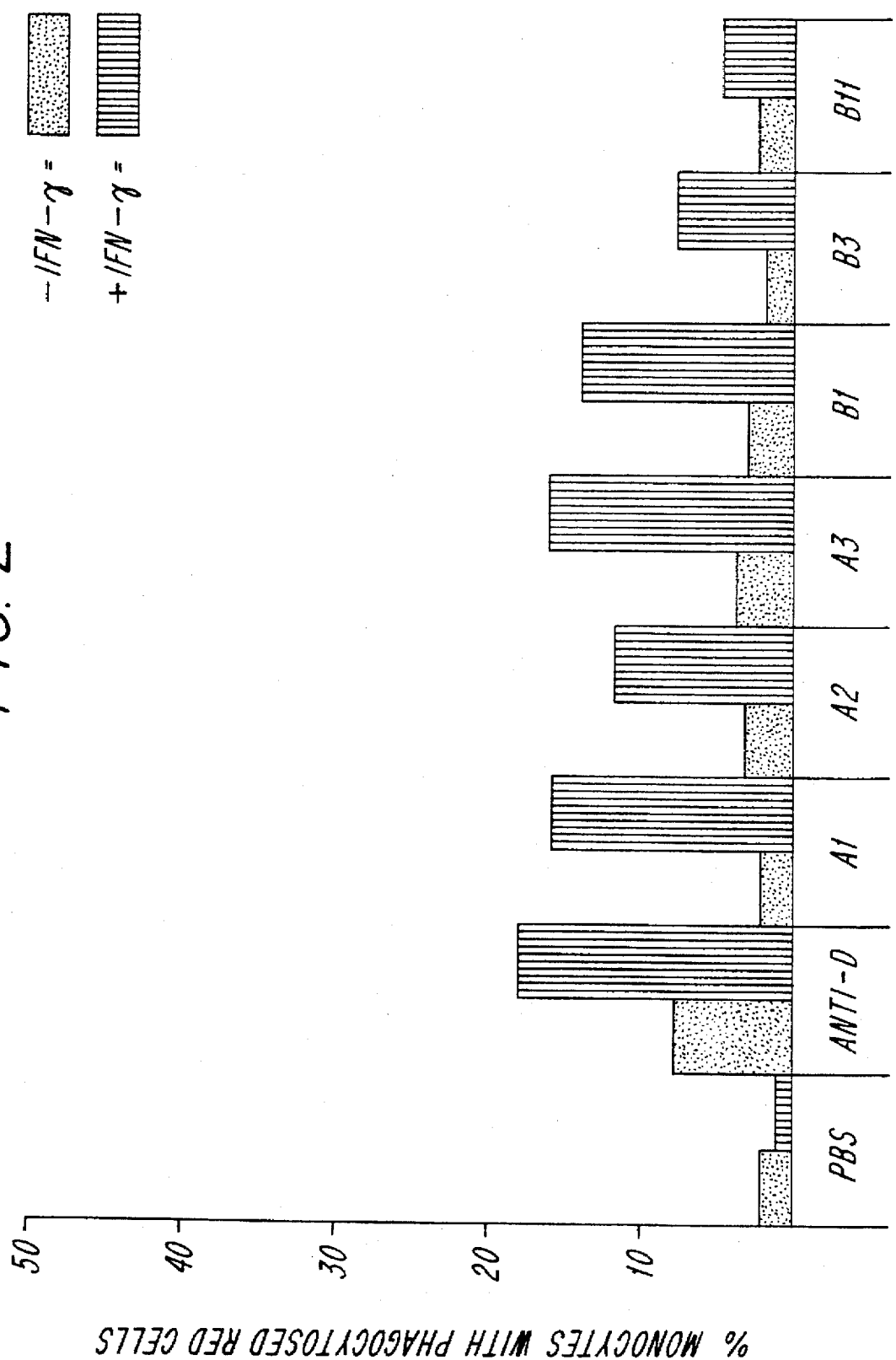
FIG. 2 is a comparison of phagocytosis results (expressed as the percentage of monocytes with one or more adherent or phagocytosed red cells) obtained with culture supernatants of clones A1, A2, A3, B1, B3 and B11 and a conventional polyclonal anti-Rh(D) serum.

A comparision of the results obtained wth culture supernatants of clones A1, A2, A3, B1, B3 and B11 and a conventional polyclonal anti-Rh(D) serum is given in FIGS. 1 and 2.

(v) Macrophage binding assay

RBCs ($R_2r$) (1 volume) were sensitised with monoclonal anti-Rh(D) (2 volumes of untreated culture supernatant) and incubated with monocyte-derived cultured macrophases. The macrophages were stimulated with 500 U/ml of recombinant immune interferon (Biogen, Geneva) during the 48 hours prior to their use in the assay. The binding of RBCs to macrophages was assessed microscopically and expressed as the macrophage binding index (=number of red cells attached to or ingested by 100 macrophages).

Table XI below shows the results obtained with culture supernatants of clones A1, A2, A3, B1, B3 and B11. The ability of these supernatants to bring about RBC-macrophage interaction was very poor compared to that of the polyclonal anti-Rh serum (anti-Rh(D)–43 IU/ml), which served as a positive control.

TABLE XI

| Source of anti-Rh(D) | A1 | A2 | A3 | B1 | B3 | B11 | polyclonal anti-Rh(D) serum. |
|---|---|---|---|---|---|---|---|
| Macrophage binding index | 20 | 28 | 24 | 5 | 20 | 17 | 416–500 |

EXAMPLE 2

Solution for Rh(D)-Phenotyping of RBCs

In general, it is preferred for the above purpose to use a blend of an anti-Rh(D) monoclonal antibody according to the invention (e.g. B11) with a further IgG monoclonal antibody having anti-$D^{VI}$ activity, for example the monoclonal antibody of the cell line B7 (ECACC-87091603) of our copending International patent application No. PCT/GB88/00756 (Publication No. WO89/02443), filed Sep. 16, 1988, the contents of which are incorporated by reference into the present specification.

Solution for Manual Use

The final blend is 1:1:1 B11:B7: diluent.

Diluent 100 ml 30% Bovine Serum Alubumin 2.42 g $KH_2PO_4$ 2.77 g $Na_2HPO_4.2H_2O$ 4.50 g NaCl 0.2 ml Tween 20

1.00 g $NaN_3$

To 1.0 liter with distilled water: pH 6.8

This blend can be used in all manual tests for D and $D^u$ typing, e.g. microtitre, microplate, IAG.

A blend of 1:1:2 B11:B7: diluent may also be used.

Blend for Machine Use

This blend may be used, for example, in a Technicon autogrouper 16C

Pre-blend reagents B11:B7 1:1

For D-Phenotyping (D-positive v. D-negative) the solution comprises 1:1000 blend: diluent, and for $D^u$ determinations ($D^u$ v. D-negative) the solution comprises 1:5 blend-:diluent.

Diluent

2% Bovine Serum Albumin in 1.3% physiological saline containing 13.5% methylcellulose.

The monoclonal antibody B7 may be similarly blended with other antibodies of the present invention, e.g. the monoclonal antibodies of the deposited cell lines A3 (ECACC 86091605) and B2 (ECACC 8609104) to provide an anti-Rh(D) reagent with broad specificity for the various D-variant antigens, including $D^{VI}$, and exhibiting activity against $D^u$ cells by an IAG test.

We claim:

1. A method of suppressing an immunogenic response, wherein said immunogenic response is an anti-D response, in an Rh(D) negative, Rh(D) variant, or Rh($D^u$) human subject, following exposure of said subject to Rh(D) positive red blood cells by transfusion or pregnancy, comprising administering to said subject a human monoclonal antibody having the following characteristics:

(a) binding to Rh(D) antigen, but not C, c, E or e antigens of the Rh blood group system;

(b) being IgG1 proteins;

(c) having kappa light chains;

(d) being Glm (3) or Glm (1, 17) allotype;

(e) binding to $D^u$ cells by the indirect antiglobulin test;

(f) binding to $D^{IV}$, $D^V$ and $D^{Tar}$ ($D^{VII}$) variant antigens; and (g) not binding to $D^{VI}$ or $D^B$ variant antigens;

or antigen-binding fragments thereof.

2. A method as claimed in claim 1, wherein the monoclonal antibody is produced by the cell line ECACC 87091604 or ECACC 87091605.

3. A method as claimed in claim 1, or claim 2, wherein the antibody is administered together with at least one further monoclonal antibody which binds the $D^{VI}$ variant antigen.

4. The method as claimed in claim 1, or claim 2 for suppressing an immunogenic response in an Rh(D) negative, Rh(D) variant or Rh(D$^u$) human female subject, comprising administering said antibody to said female subject following delivery of a Rh(D) positive baby.

5. The method as claimed in claim 1, or claim 2 for suppressing an immunogenic response in an Rh(D) negative, Rh(D) variant, or Rh(D$^u$) human female subject, comprising administering said antibody to said female subject during pregnancy.

6. A method of suppressing an immunogenic response, wherein said immunogenic response is an anti-D response, in an Rh(D) negative, Rh(D) variant, or Rh(D$^u$) human subject, following exposure of said subject to Rh(D) positive red blood cells by transfusion or pregnancy, comprising administering to said subject a human monoclonal antibody having the following characteristics:

(a) binding to Rh(D) antigen, but not C, c, E or e antigens of the Rh blood group system;

(b) being IgG1 proteins;

(c) having kappa light chains;

(d) being Glm (3) or Glm (1, 17) allotype;

(e) binding to $D^u$ cells by the indirect antiglobulin test;

(f) binding to $D^{IV}$, $D^V$ and $D^{Tar}$ ($D^{VII}$), variant antigens; and (g) not binding to $D^{VI}$ or $D^B$ variant antigens;

or antigen-binding fragments thereof, in combination with at least one anti-Rh(D) monoclonal antibody of the IgG3 subclass.

7. A method as claimed in claim 6, wherein the monoclonal antibody having the characteristics (a–g) is produced by the cell line ECACC 87091604 or ECACC 87091605.

8. A method as claimed in claim 6 or 7, wherein the antibody having the characteristics (a–g) is administered together with at least one further monoclonal antibody which binds the $D^{VI}$ variant antigen.

9. A method as claimed in claim 6 or 7, wherein the IgG3 anti-Rh(D) monoclonal antibody is produced by the cell line ECACC 87091606.

10. A method as claimed in claim 6 or 7, wherein the composition is administered to a human female subject following delivery of a Rh(D) positive baby.

11. A method as claimed in claim 8, wherein the composition is administered to a human female subject following delivery of a Rh(D) positive baby.

12. A method as claimed in claim 9, wherein the composition is administered to a human female subject following delivery of a Rh(D) positive baby.

13. A method as claimed in claim 6 or claim 7, wherein the composition is administered to a human female subject during pregnancy.

14. A method as claimed in claim 8, wherein the composition is administered to a human female subject during pregnancy.

15. A method as claimed in claim 9, wherein the composition is administered to a human female subject during pregnancy.

16. A method of passive immunization to prevent haemolytic disease of the newborn, comprising administering to an Rh(D) negative, Rh(D) variant, or Rh(D$^u$) human female a human monoclonal antibody having the following characteristics:

(a) binding to Rh(D) antigen, but not C, c, E or e antigens of the Rh blood group system;

being IgG1 proteins;

(c) having kappa light chains;

(d) being Glm (3) or Glm (1, 17) allotype;

(e) binding to $D^u$ cells by the indirect antiglobulin test;

(f) binding to $D^{VI}$, $D^V$ and $D^{Tar}$ ($D^{VII}$) variant antigens; and (g) not binding to $D^{VI}$ or $D^B$ variant antigens;

or antigen-binding fragments thereof.

17. A method as claimed in claim 16, wherein the monoclonal antibody is produced by the cell line ECACC 87091604 or ECACC 87091605.

18. A method as claimed in claim 16 or claim 17, wherein the antibody is administered together with at least one further monoclonal antibody which binds the $D^{VI}$ variant antigen.

19. A method of passive immunization to prevent haemolytic disease of the newborn, comprising administering to an Rh(D) negative, Rh(D) variant, or Rh(D$^u$) human female a human monoclonal antibody having the following characteristics:

(a) binding to Rh(D) antigen, but not C, c, E or e antigens of the Rh blood group system;

being IgG1 proteins;

(c) having kappa light chains;

(d) being Glm (3) or Glm (1, 17) allotype;

(e) binding to $D^u$ cells by the indirect antiglobulin test;

(f) binding to $D^{IV}$, $D^V$ and $D^{Tar}$ ($D^{VII}$) variant antigens; and (g) not binding to $D^{VI}$ or $D^B$ variant antigens;

or antigen-binding fragments thereof, in combination with at least one anti-Rh(D) monoclonal antibody of the IgG3 subclass.

20. A method as claimed in claim 19, wherein the monoclonal antibody having the characteristics (a–g) is produced by the cell line ECACC 87091604 or ECACC 87091605.

21. A method as claimed in claims 19 or 20, wherein the antibody having the characteristics (a–g) is administered together with at least one further monoclonal antibody which binds the $D^{VI}$ variant antigen.

22. A method as claimed in claim 19 or claim 20, wherein the Iga3 anti-Rh(D) monoclonal antibody is produced by the cell line ECACC 87091606.

23. The method as claimed in claim 3 for suppressing an immunogenic response in an Rh(D) negative, Rh(D) variant or Rh(D$^u$) human female subject, comprising administering said antibody to said female subject following delivery of a Rh(D) positive baby.

24. The method as claimed in claim 3 for suppressing an immunogenic response in an Rh(D) negative, Rh(D) variant, or Rh(D$^u$) human female subject, comprising administering said antibody to said female subject during pregnancy.

* * * * *